United States Patent
Panchal et al.

(10) Patent No.: US 9,796,656 B1
(45) Date of Patent: Oct. 24, 2017

(54) METHOD OF PRODUCING HIGH-CONCENTRATION ALKYL CARBONATES USING CARBON DIOXIDE AS FEEDSTOCK

(71) Applicant: E3TEC SERVICE, LLC, South Barrington, IL (US)

(72) Inventors: Chandrakant B. Panchal, South Barrington, IL (US); John C. Prindle, Baton Rouge, LA (US)

(73) Assignee: E3TEC Service, LLC, South Barrington, IL (US)

( * ) Notice: Subject to any disclaimer, the term of this patent is extended or adjusted under 35 U.S.C. 154(b) by 0 days.

(21) Appl. No.: 15/345,698

(22) Filed: Nov. 8, 2016

Related U.S. Application Data (62) Division of application No. 14/445,992, filed on Jul. 29, 2014, now Pat. No. 9,518,003.

(60) Provisional application No. 61/958,515, filed on Jul. 30, 2013.

(51) Int. Cl.
    *C07C 68/08* (2006.01)
(52) U.S. Cl.
    CPC .................... *C07C 68/08* (2013.01)
(58) Field of Classification Search
    CPC .................................... C07C 68/08
    See application file for complete search history.

(56) References Cited

U.S. PATENT DOCUMENTS

| | | |
|---|---|---|
| 4,661,609 A | 4/1987 | Knifton |
| 4,691,041 A | 9/1987 | Duranleau et al. |
| 4,734,518 A | 3/1988 | Knifton |
| 5,359,118 A | 10/1994 | Wagner |

OTHER PUBLICATIONS

Wang, F., N. Zhao, J. Li, W. Zhao, F. Xiao, W. Wei, and Y. Sun, Modeling of the Catalytic Distillation Process for the Synthesis of Dimethyl Carbonate by Urea Methanolysis Method, Ind. Eng. Chem. Res., 46, pp. 8972-8979 (2007).
Yang, B., D. Wang, H. Lin, J. Sun, and X. Wang, Synthesis of Dimethyl Carbonate from Urea and Methanol Catalyzed by the Metallic Compounds at Atmospheric Pressure, Cat. Commun., 7, pp. 472-477 (2006).
Fang, Y-J. and W-D. Xiao, Experimental and Modeling Studies on a Homogeneous Reactive Distillation System for Dimethyl Carbonate Synthesis by Transesterification, Separation and Purification Technology, 34, pp. 255-263 (2004).
Ahn, B.S., M.S. Han, Y.J. Lee and H. Abimanyu, Transesterification Between Methanol and Ethylene Carbonate Over Fixed-Bed K/MgO Catalyst for Reactive Distillation, Proceedings of 4th International Conference on Separation Science and Technology, Z. Tong and S-H. Kim (eds), pp. 329-333 (2004).
Shangguan N, Principal Investigator, Membrane Facilitated Dimethyl Carbonate Production from Carbon Dioxide, SBIR Phase 1 2013, Abstract, Compact Membrane Systems Inc., Newport, NJ, USA, DOE Contract DE-F602-13ER90644 (2013).
Won, W., Feng, X, and Lawless, D, PerVaporation with Chitosan Membranes: separation of Dimethyl Carbonate/Methanol/Water Mixtures, Journal of Membrane Science, 209, 493-508 (2002).
Won, W., Feng, X, and Lawless, D, Separation of Dimethyl/Methanol/Water Mixtures by PerVaporation using Cross-Linked Membranes, Separation Purification Technology, 31, 129-140 (2003).

*Primary Examiner* — Shawquia Jackson
(74) *Attorney, Agent, or Firm* — Rosenberg, Klein & Lee (57) ABSTRACT

A method of producing high purity dimethyl carbonate through the reaction of carbon dioxide and methanol is provided. In the ammonia-based method ammonia and carbon dioxide react to produce urea. The urea is mixed with methanol for further reaction to produce dimethyl carbonate. Ammonia released in the process is recycled as a reactant to produce more urea. It is then reacted with methanol to produce dimethyl carbonate. An integrated reactive distillation process using side reactors is used for facilitating catalytic reaction in the method for producing high purity dimethyl carbonate. The process is further enhanced by enclosing multiple side reactors into a pressure vessel and incorporating thermal heat pump for recovery and reuse of latent heat within the process.

12 Claims, 8 Drawing Sheets

| | Name | Refrigerant | Absorbents | Typical Operating Temperatures | | Temp Lift - Single stage | Property Sources | Characterization |
|---|---|---|---|---|---|---|---|---|
| | | | | High C | Low C | C | | |
| A | NH3-H2O | Ammonia | Water | 120 | -28 | 30 to 50 | Widely available & Aspen+ | Ideal working fluid pair, provided it can be used for temperature ranges and environmental concerns. |
| B | LiBr-H2O | Water | Lithium Bromide | 100 | 6 | 20 to 30 | Widely available & Aspen+ | Can be used in a narrow range of temperatures due to crystallization and corrosion issues. |
| C | Alkitrate | Water | Alky salts of nitrates | 200 | 100 | > 50 | Limited & Aspen+ | Specifically for higher temperature and temperature lift. |
| D | Ionic Fluid A | Trifluoro ethanol (TFE) | 1-Butyl Imidazolium tetrafluoro borate ([BMIm][BF4]) | 200 or higher | TBD | > 50 | Limited source of properties | Emerging working fluids with advantageous thermodynamic and physical properties. |
| E | Ionic Fluid B | Trifluoro ethanol (TFE) | 1-Butyl 3-Methyl Imidazolium bromide ([BMIm][Br]) | 200 or higher | TBD | > 50 | Limited source of properties | Emerging working fluids with advantageous thermodynamic and physical properties. |
| F | Ionic Fluid C | Methanol | 1-ethyl 3-methyl imidazolium acetate | 200 or higher | 5 | > 50 | Limited source of properties | Emerging working fluids with advantageous thermodynamic and physical properties. |
| G | Organic A | R134a | Dimethylether Diethylene Glycol | 200 or higher | 0 | > 50 | Aspen+ | Less favorable thermodynamic and physical properties. Can be considered as an alternate working fluid pair. |
| H | Organic B | R134a | Dimethylether Triethylene Glycol | 200 or higher | 0 | > 50 | Aspen+ | Less favorable thermodynamic and physical properties. Can be considered as an alternate working fluid pair. |

| Process Unit | Heat Rejected and Recovered kW | Inlet Temperature °C | Outlet Temperature °C | Heat Recovery Process using Thermal Heat Pump |
|---|---|---|---|---|
| Reactor products | 2,026 | 127 | 100 | Preheating feed |
| Distillation overhead | 3,508 | 77 | 77 | Preheating feed |
| Distillation overhead | 1,842 | 118 | 118 | Preheating feed and/or internal reboiler using thermally active trays |
| Bottom product | 711 | 120 | 120 | Preheating feed and/or internal reboiler using thermally active trays |

METHOD OF PRODUCING HIGH-CONCENTRATION ALKYL CARBONATES USING CARBON DIOXIDE AS FEEDSTOCK

REFERENCE TO RELATED APPLICATIONS

This Application is a Divisional Application of Ser. No. 14/445,992, filed on 29 Jul. 2014, which is based upon Provisional Patent Application 61/958,515 filed on 30 Jul. 2013.

FIELD OF THE INVENTION

The subject invention relates to reactive distillation for the manufacture of industrial chemicals. In overall concept the subject system and method relates to the production of alkyl carbonates using an alcohol and captured carbon dioxide from industrial processes. In particular, this invention relates to a method of producing concentrated dimethyl carbonate compositions. Additionally, this application is directed to the field of producing concentrated dimethyl carbonate compositions in a reactive distillation process. This invention is further directed to the field of the production of concentrated dimethyl carbonate composition with side products being drawn from the reactive distillation recycling process.

BACKGROUND OF THE INVENTION

Alkyl carbonates form an important building block or component in many commercial products. In particular, dimethyl carbonate is a commercial methylating agent which replaces other reagents such as phosgene, iodomethane, and dimethyl sulfate. These generally are more toxic than dimethyl carbonate and less biodegradable. The alkyl carbonate in combination with other alkyl carbonates is a major component of electrolyte solutions in lithium ion batteries since the high polarity of alkyl carbonate solutions allows them to dissolve within the lithium salts. Dimethyl carbonate has been exempted from the definition of volatile organic compounds which allows fabricators to use dimethyl carbonate as coating, cleaning, and adhesive solvents as a replacement for defined volatile organic compounds. Dimethyl carbonate may replace the gasoline oxygenate methyl t-butyl ether due to its high oxygen content, biodegradability characteristics and low toxicity. The dimethyl carbonate has been found to improve combustion and emission performance when used as a diesel fuel additive.

PRIOR ART

Alkyl carbonates have previously been produced by reacting the alcohol with phosgene. However, due to the toxicity of phosgene, this process route is being displaced by the oxidative gas or liquid phase carbonylation of the alcohol with carbon monoxide over a copper (II) chloride catalyst. The carbonylation using methanol as the alcohol follows the chemical process:

$$2CH_3OH + \tfrac{1}{2}O_2 + CO_2 \rightarrow (CH_3O)_2CO + H_2O \quad (1)$$

Further prior art commercial practices are directed to a two-step gas-phase reaction of alcohol with methylnitrite. An initial step in the production of the nitrite from the requisite alcohol, nitrogen oxides and oxygen are used. The alkyl carbonate is then produced by reaction of the methyl nitrite with carbon monoxide as the alkyl carbonate. The NO produced with the alkyl carbonate is recovered and recycled. Using methanol as the alcohol, the process is shown in equations (2), (3) as follows:

$$2NO + \tfrac{1}{2}O_2 \rightarrow N_2O_3 \quad (2)$$

$$2CH_3OH + N_2O_3 \rightarrow 2CH_3ONO + H_2O \quad (3)$$

Obtaining the process using dimethyl carbonate as the alkyl carbonate is shown in Eq. 4 as follows:

$$2CH_3ONO + CO \rightarrow (CH_3O)_2CO + 2NO \quad (4)$$

Generally, the first step of the process is conducted without a catalyst whereas the second step is carried out in the presence of a catalyst such as palladium chloride.

Both of the prior art known commercial processes require reaction mixtures of oxygen with methanol which creates a potentially explosive mixture. Both of the prior art commercial processes indicated above require the production of syngas (CO/H$_2$) which also generates carbon dioxide as a byproduct.

Reactive distillation has been studied for the production of dimethyl carbonate from both heterogeneous and homogeneous catalytic processes using ethylene carbonate and methanol as feedstock. However, only homogeneous catalysts have been reported to provide high conversion at reasonable operating conditions and catalyst separation makes them uneconomical in an industrial process. Heterogeneous catalysts result in low conversions at conventional reactive distillation conditions requiring either higher methanol/ethylene carbonate molar ratios or higher reaction temperatures to achieve high conversions. Larger molar ratios increase equipment size while higher temperatures may only be achieved by operating at higher pressures. Either alternative would result in increased capital costs for conventional reactive distillation processes. In addition, higher temperatures have been reported to result in side reactions forming polyols and other undesired by-products.

Dimethyl carbonate and methanol form a homogeneous azeotropic composition mixture over a wide range of pressures which makes it difficult to separate the components without the addition of a third component as an entrainer. The processes as herein described and claimed operate in a manner that permits the separation of dimethyl carbonate from the other components in the system devoid of the need of an entrainer.

The subject system and method decouples the reaction temperature/pressures from those which are optimal for separation which allows a higher reaction temperature and conversion without the need for higher pressures and capital expenditures for the separation equipment. The side reactors as described, permit greater catalyst loadings in the reaction zone than is known for conventional reactive distillation. The side reactors provide for optimal reaction conditions permitting significant reduction in excess alcohol. The processes as herein described achieve high conversions with greater energy efficiency at molar ratios in the 3-6 range. Through the incorporation of a pervaporation membrane unit in the separation step, the dimethyl carbonate/methanol azeotrope is overcome without the need of any entrainer.

SUMMARY OF THE INVENTION

In one process as herein described, there is provided the method of producing a concentrated dimethyl carbonate composition by reacting carbon dioxide and ammonia to form an ammonium carbamate in a reaction tank and further forming urea. The urea and methanol are mixed in the stirring tank and the resulting mixture is inserted into a prereactor to produce methyl carbamate and ammonia. The methyl carbamate and ammonia is reacted with methanol to produce a dimethyl carbonate and ammonia mixture. The mixture is then inserted into a divided wall distillation column having a first distillation column section and a second distillation column section. The first distillation column section is charged with unreacted methyl carbamate, unreacted methanol, dimethyl carbonate, and ammonia mixture and there is a recycling of the ammonia from the first distillation column section to the ammonium carbamate reaction tank.

A mixture of dimethyl carbonate and methyl carbamate with unreacted methanol is drawn from a first stage of the first distillation column first section and passed through a side reactor and producing a more concentrated dimethyl carbonate composition. The concentrated dimethyl carbonate is then returned to the distillation column and a still further concentrated dimethyl carbonate composition is drawn from a lower section of the distillation column.

An alternative process for providing concentrated dimethyl carbonate, carbon dioxide and ethylene oxide are reacted in a reaction chamber to produce an ethylene carbonate composition. A methanol side reactor is charged with the ethylene carbonate composition to produce a composition containing dimethyl carbonate, ethylene glycol and unreacted methanol as well as some unreacted ethylene carbonate. The composition is then inserted into a distillation column in an upper section and purified dimethyl carbonate composition is withdrawn from the upper section of the distillation column along with unreacted methanol. Ethylene glycol and ethylene carbonate are accumulated in a lower section of the distillation column and the ethylene glycol and ethylene carbonate are purified to produce an ethylene glycol rich composition as a byproduct.

An object of the subject invention is to provide an energy-efficient and environmentally-friendly process which manufactures alkyl carbonates from carbon dioxide and the requisite alcohol results in a net consumption of carbon dioxide.

A further object of the subject system and process is to provide a process which produces alkyl carbonates at high alcohol conversions and alkyl carbonate selectivity with a minimization of any capital expenditures.

A further object is to provide an alkyl carbonate process permitting efficient separation of the resulting alkyl carbonate alcohol product mixtures without needs for any entrainers.

The ammonia-based process for producing concentrated dimethyl carbonate using an initial reaction of carbon dioxide and ammonia to form ammonium carbamate which includes initially reacting ammonia with carbon dioxide to produce urea where water is the byproduct and the chemical pathway is as shown in Equation (5) as follows:

$$2NH_3 + CO_2 \leftrightarrow NH_2COO^-NH_4^+ + \leftrightarrow NH_2CONH_2 + H_2O \qquad (5)$$

The urea and requisite alcohol in this case in the form of methanol is converted into the alkyl carbonate, such as dimethyl carbonate and ammonia using a reactive distillation process where the chemical pathway is shown in Equation (6) as follows:

$$(6)$$

Ammonia is separated from the excess alcohol and recycled for producing additional urea. Thus, the urea and reactive distillation processes are integrated for an energy efficient total process of dimethyl carbonate production from methanol and carbon dioxide with ammonia being the reaction carrier. In an integrated process, the urea does not have to be produced in the form of crystals, but in a concentrated solution with carryover water being used as a feedstock. In this manner, the energy consumption is reduced by not concentrating and crystallizing the urea.

With the energy estimates from commercial urea production facilities coupled with those from the alkyl carbonate process, it is believed that the proposed process with the inclusion of the urea portion for manufacturing dimethyl carbonate would consume 0.49 kg per kg of dimethyl carbonate with emission of 0.21 kg per kg of dimethyl carbonate production. Thus, this process has potential of permanent sequestration of 0.28 kg of carbon dioxide ($CO_2$) into high-value product. The table below represents process parameters of a typical commercial plant cited in FIG. 2 with production capacity of 50,000 metric tons per year with product purity of 99.8 wt %.

Figure 2:
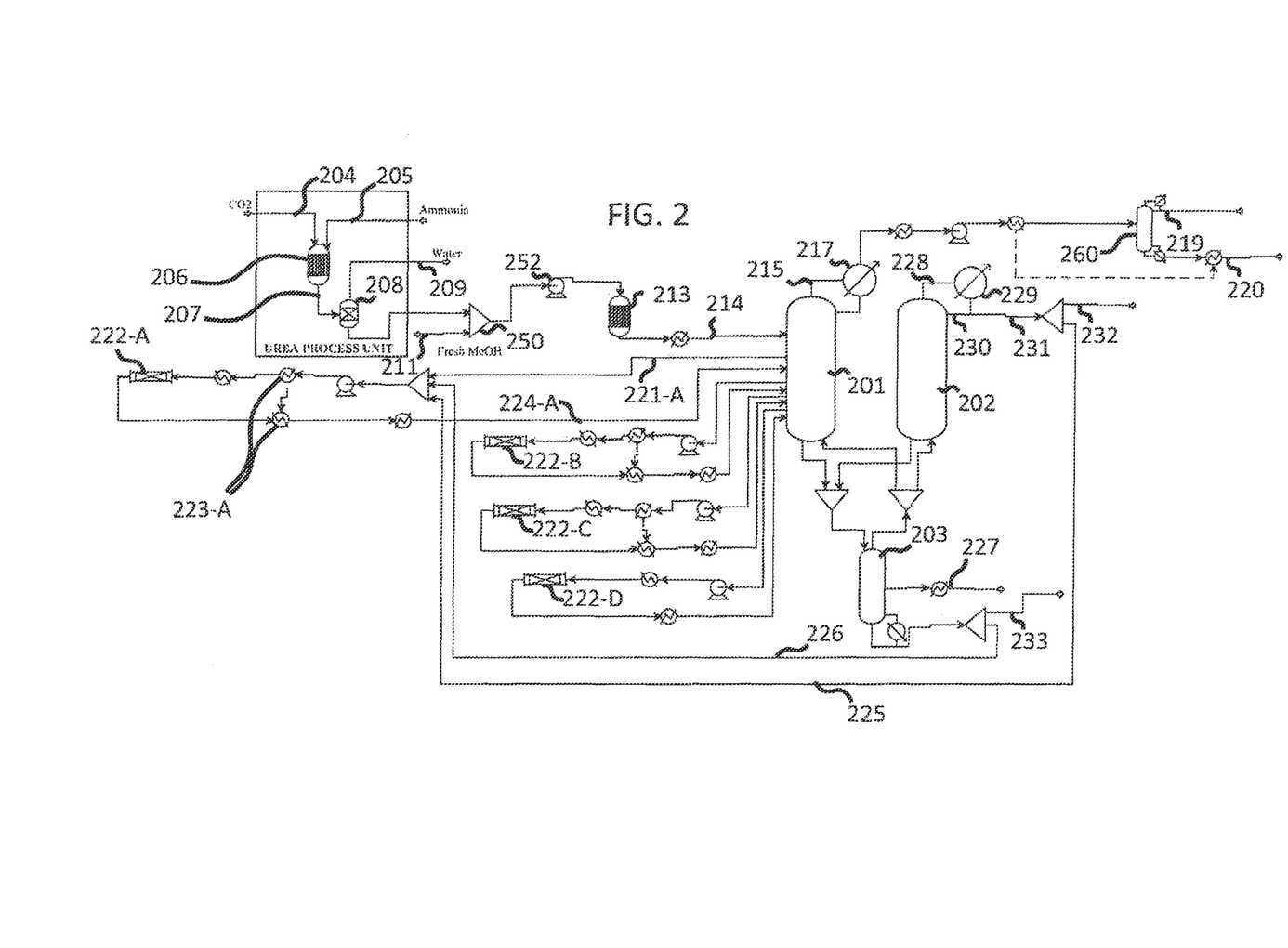
FIG. 2 is a commercial flow schematic diagram based upon the ammonia based alkyl carbonate processing flow.

| Process Parameter | Value | Units |
|---|---|---|
| Dimethyl Carbonate (DMC) | 6,250 | kg/hr |
| Production Capacity | 50,000 | metric tons/year |
| Pure DMC | 6,238 | kg/hr |
| DMC Concentration | 99.8% | wt % |
| Product yield based on $CO_2$ Feedstock | 97% | |
| Captured $CO_2$ | 3,144 | kg/hr |
| Fresh Methanol Flow Rate Side Reactors | 4,715 | kg/hr |
| Temperature | 170 C. | |
| Pressure | 27 bar | |
| Divided-Wall Distillation column | | |
| Reflux temperature | ~80 C. and 120 C. | |
| Bottom temperature | ~250 C. | |
| Energy Consumption | | |
| Thermal heat input | 10,854 | kW |
| Heat rejection | 8,087 | kW |
| Fraction reject heat recovery | 0.60 | |
| Effective heat recovery | 4,852 | kW |
| Net energy consumption | 6,002 | kW |
| CO2 Merit Value | | |
| $CO_2$ Consumed | 0.49 | kg $CO_2$/kg DMC |
| $CO_2$ Generated by the process | 0.21 | kg $CO_2$/kg DMC |
| $CO_2$ Merit Value = Consumed/Generated | 2.33 | |

The ethylene oxide-based process is based on chemical pathways of carbon dioxide reacting with ethylene oxide to produce ethylene carbonate where the ethylene carbonate is reacted with the requisite alcohol to produce the alkyl carbonate and ethylene glycol, as is depicted in equations (7) and (8) as follows:

$$(7)$$

$$(8)$$

Both of the above chemical processes incorporate the use of conventional reactive distillation with side reactors to simultaneously achieve high alcohol conversion and alkyl carbonate selectivity. The side reactors in both of the processes are used for conducting the majority of the reaction and are operated at higher temperatures, pressures and catalyst loadings than the separation section which may include either a distillation column either divided wall or conventional, or a reactive distillation column. Such high temperatures and pressure conditions and catalyst loadings are localized to smaller equipment of the side reactors which permit lower capital expenditures.

BRIEF DESCRIPTION OF THE DRAWINGS

FIG. 7 is a representation of different absorbent pairs and parameters associated therewith that may be used in the heat pump system; and, FIG. 8 is a representation of the heat pump process indicating the showing of thermal and electrical parameters associated with the heat pump design.

DESCRIPTION OF THE PREFERRED EMBODIMENTS

Referring now to FIGS. 1-4, there is described a process for producing purified and concentration dimethyl carbonate.

As shown in FIGS. 1-4, the method and system consists of a reactive distillation based process which is an ammonia based process configuration.

Figure 1:
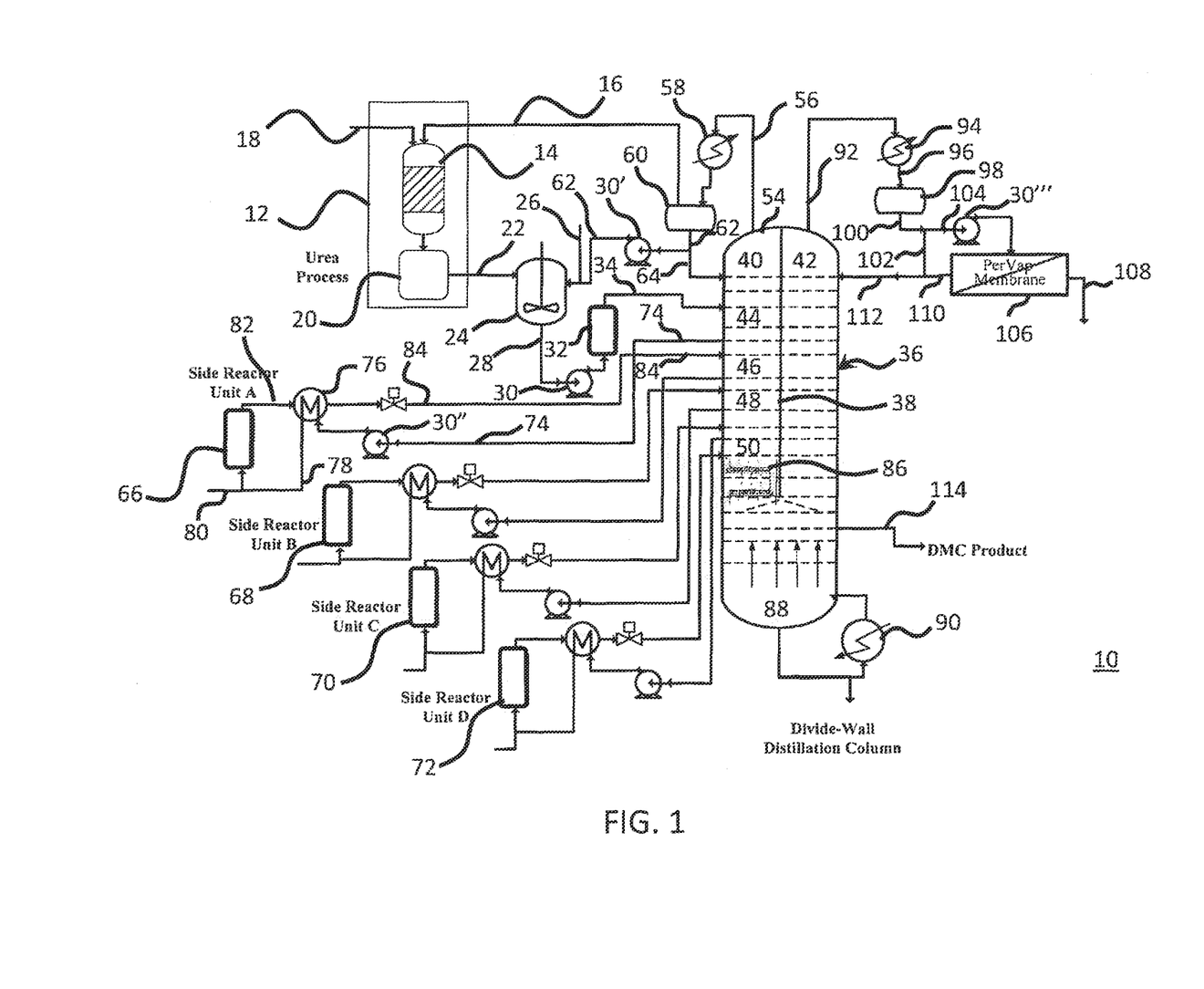
FIG. 1 is a schematic process flow diagram for an ammonia-based alkyl carbonate process.

Referring now to FIG. 1, ammonia based distillation system 10 includes a plurality of recycling components and steps which results in a purified and concentrated dimethyl carbonate composition exiting from a partitioned distillation column 36 on dimethyl carbonate product line 114. The system as shown in FIG. 1 is for the synthesis of alkyl carbonate using captured carbon dioxide and alcohol (methanol). Synthesis of dimethyl carbonate using captured carbon dioxide as a model process is presented, however, the system and method is applicable for synthesis of other organic carbonates, such as diethyl carbonate, sequences of analogs using alcohols of higher molecular weights and mixed alkyl carbonates using different alcohols in the process system.

As shown in FIG. 1, recycled ammonia is fed on recycled ammonia feed line 16 in combination with carbon dioxide fed into first reaction tank 14 through line 18 which is part of the reaction system 12. The carbon dioxide and ammonia react within first reaction tank 14 to produce urea and water which is then fed to urea crystallization process unit 20 where the urea may be further concentrated using a commercially known multi-effect evaporator and crystallization produces urea in crystal form which is inserted through urea feed line 22 to stirring tank 24. A more preferred embodiment would only partially concentrate the urea up to the point of crystallization removing the remaining water by vapor stripping with methanol and leaving a methanol/urea solution substantially free of water.

Methanol is inserted into stirring tank 24 on methanol feed line 26 to produce a uniform composition of urea and methanol on line 28. The composition is then pumped through pump 30 to a pre-reaction catalytic reactor 32 which may be a methanol reactor to produce substantially a dimethyl carbonate, ammonia, unreacted methanol and unreacted methyl carbamate discharge on feed line 34. The product stream being transported on feed line 34 is inserted or fed into partitioned distillation column 36 which has a plurality of distillation stages 44, 46, 48, 50, as will be described in following paragraphs. Ammonia and methanol accumulates in upper section 54 of first distillation column section 40. The ammonia and methanol vapor is drawn through ammonia and methanol feed line 56 to condenser 58 which may be a water or air-cooled condenser commercially available. The condensate along with some uncondensed ammonia vapor is collected in receiver tank 60 where the ammonia is separated from the methanol from the distillate stream and returned on recycled ammonia feed line 16 to reaction tank 14 for further processing. A more preferred embodiment would further purify the ammonia in stream 16 by distillation before recycling it back to the urea process.

Methanol exits from receiver tank 60 and is re-inserted into stirring tank 24 through pump 30' and methanol feed line 62. Some methanol may be re-inserted into first distillation column section 40 of the partitioned distillation column 36 on feed line 64.

The methyl carbamate is converted to dimethyl carbonate by way of the multiple side reactors 66, 68, 70, and 72. It is to be understood that more or less side reactors may be used and only one flow process for one of the side reactors will be further described for the sake of brevity and clarification.

With respect to the process associated with side reactor 66, it is seen that a product stream is drawn from one stage of the partitioned distillation column 36 which flows through product streamline 74 to pump 30" which inserts the product stream into heat exchanger 76 which may recover heat from product streams for pre-heating the feed for improving energy efficiency of the overall product. Subsequent to passage of the product stream through heat exchanger 76, the product stream is inserted into methanol side reactor 66 on line 78. The product stream subsequent to heating on line 78 may be combined with additional methanol being input through additional methanol line 80 for insert into side reactor 66. The methyl carbamate is then converted to dimethyl carbonate and exits on product line 82 for passage through heat exchanger 76 for re-entry into partitioned distillation column 36 on line 84. The conversion to the product may further be enhanced by the use of reactive distillation stages 86 with only one reactive distillation stage 86 being shown for the purposes of clarification. Catalysts on reactive distillation stages 86 may either be incorporated on distillation trays or packed columns. As is seen in FIG. 1, the product stream returning on re-entry product lines 84 are inserted into distillation column 36 one stage lower than the withdrawal stage represented by product stream line 74.

A product rich mixture or composition thus accumulates in the bottom portion 88 of the distillation column 36 subsequent to passage through stages 42, 44, 46, 48, and possibly a reactive distillation stage or stages 86. Dimethyl carbonate along with some unreacted methanol is vaporized through well-known heaters 90 for passage of the dimethyl carbonate along with the unreacted methanol through the second distillation column section 42 where methanol and dimethyl carbonate form an azeotrope which generally cannot be separated using conventional distillation processes. The dimethyl carbonate and methanol composition exits distillation column 36 on dimethyl carbonate and methanol line 92 for insert into condenser 94. The overhead vapor stream of dimethyl carbonate and methanol after being condensed in condenser 94 is inserted on line 96 to receiver tank 98. A receiver tank output line 100 is split into dimethyl carbonate rich line 102 and line 104 for passage through pump 30′′′ for entry into pervaporation membrane system 106. Pervaporation membrane system 106 is used for breaking the azeotrope. As is known, the pervaporation membrane system 106 produces a methanol rich permeate stream on line 108 and returns a dimethyl carbonate rich stream or retentate stream on lines 110 and 112 to the distillation column 36.

Due to the recycling of the product stream as well as the ammonia, a cycling process is accomplished as previously described to produce a highly purified dimethyl carbonate composition which is withdrawn from distillation column 36 on dimethyl carbonate product line 114.

FIG. 2 is represents a simulation of a commercial installation of the basic system provided in the process flow of FIG. 1 without a pervaporation membrane system 106. In this installation schematic diagram, the partitioned distillation column is represented by the columns 201, 202, and 203. A captured carbon dioxide product stream 204 is reacted with a recycled ammonia stream on line 205 for reaction within the urea reactor 206. The reacted composition passes through the product stream line 207 for entry into the separation unit 208 for removal of water on line 209. The concentrated urea stream exits from the separation unit 208 on line 210 and is dissolved in a methanol stream 211 being inserted into combiner 250. The reacting stream is fed through pump 252 and is fed to the pre-reactor 213 with the reacted stream exiting on line 214 for insert into an upper section of distillation column 201. This substantially mirrors the flow path as provided in FIG. 1 to provide a methyl carbamate, unreacted methanol, and ammonia mixture. The reactant stream on line 214 is fed to column 201.

A volatile methanol and ammonia mixture flows upwardly through line 215 with the partially reacted product stream flowing downwardly within column 201. The vapor stream 215 carrying a mixture of methanol and ammonia is then condensed in the condenser 217 by a reflux exiting condenser 217 and is re-inserted into column 201. Rectifier 260 separates the ammonia and the methanol to respectively be removed on ammonia line 219 and methanol line 220. Ammonia on line 219 may then be recycled and combined with ammonia on ammonia line 205 for re-entry into reactor 206.

As shown in FIG. 2, side reactors 222-A, 222-B, 222-C, and 222-D may be used for the full conversion of the product. The process stream 221-A is drawn from the left side of the distillation column 201 and mixed with recycled methanol rich streams being inserted on methanol rich stream line 225 from the upper section or top of the right side of distillation column 202 and the stream 226 from the bottom product exiting distillation column 203. The mixed stream on lines 221-A, 226, and 225 is then pumped to a heat exchanger and then pre-heated in the heat exchanger 223-A and fed to the side reactor 222-A.

The product stream 224-A is then returned to column 201 one stage down from the withdrawal on line 221-A.

A product-rich stream flows down the simulated bottom column 203 and the final product stream is taken from column 203 on final product stream line 227.

The high concentration of the product stream is achieved by the distillation of simulated right side column 202 of the distillation column where the overhead stream 228 is condensed in the condenser 229 and reflux stream 230 is provided. The remaining stream is passed on line 231 for division into methanol rich stream line 225 and the composition on line 232 is processed separately for recovery of product and reactants. A purge stream 233 from a bottom section of column 203 may be used for purging undesired side products.

Figure 3:
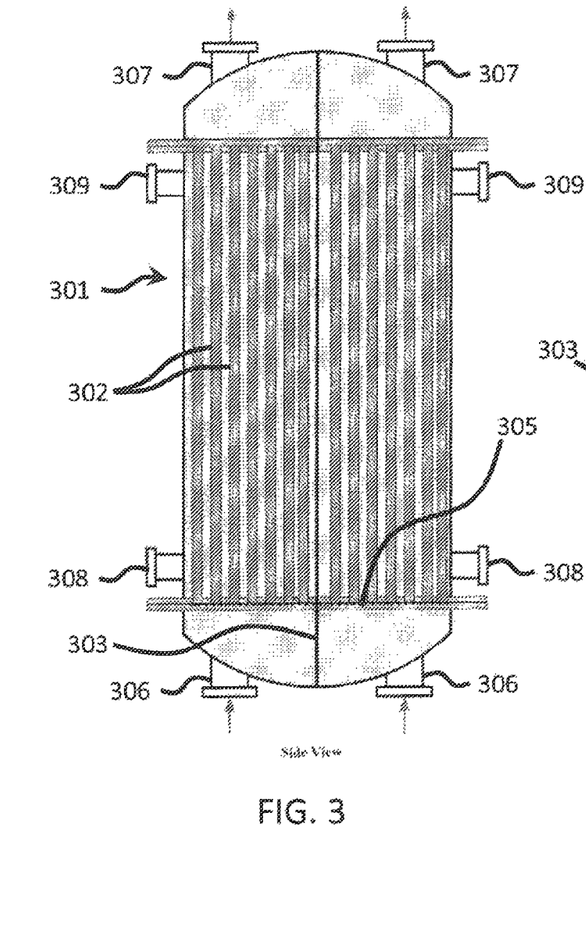
FIGS. 3-3A are schematic drawings of an integrated side reactor process unit.
Figure 3A:
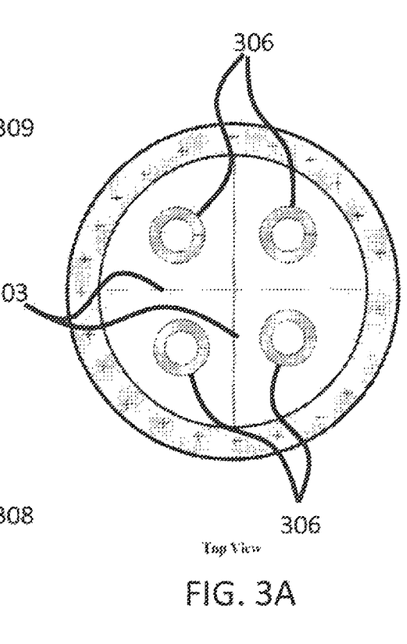

As shown in FIG. 1, a plurality of side reactors 66, 68, 70, and 72 are provided. However, an embodiment is shown in FIG. 3 showing an integrated side reactor 301 where multiple side reactors are housed in a single or multiple pressure vessel dependent upon the number of side reactors being used. The dimethyl carbonate process shown in FIG. 1 has four side reactors and in FIG. 3 all are enclosed in a single vessel 301. As seen in FIGS. 3 and 3A, multiple tubes 302 are provided where the four side reactors are divided by the partition 303 shown in FIG. 3A with each of the reactors having separate inlet nozzles 306, and outlet nozzles 307. As can be understood, reactor temperatures may be maintained by heating or cooling media circulated in an outer shell through inlet nozzles 308 and outlet nozzles 309. If desired, separate heating/cooling media may be applied by installing a partition on the shell 301 which is well-known to shell and tube heat exchanger designs.

Catalysts may be loaded from the top on the tube side with catalyst singular or multiple supports 305 mounted at a bottom flange joint. Catalysts may be loaded by feeding from the top as free catalysts or the insertion of a cartridge. Use of a cartridge catalyst provides for vision to pull catalysts from the top for replacement and provide support for using multiple cartridges in one tube.

Figure 4:
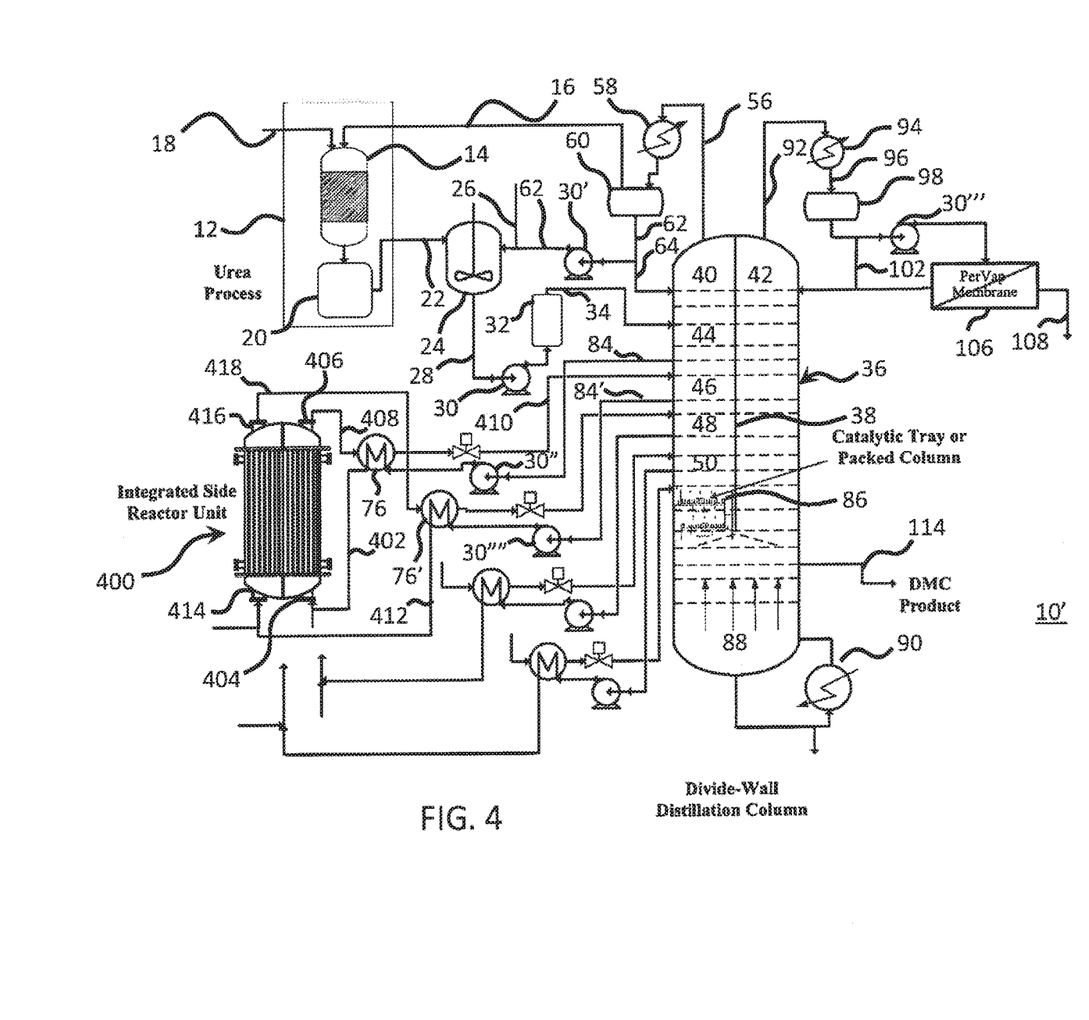
FIG. 4 is a schematic process flow diagram incorporating the integrated side reactor process unit shown in FIG. 3 for the ammonia based alkyl carbonate process.

FIG. 4 represents a system as described in FIGS. 1 and 2 where an integrated side reactor 400 is substituted for the side reactors 66, 68, 70, and 72 shown in FIG. 1. Like elements numbers in FIG. 4 are provided for common elements. In FIG. 4, the integrated side reactor unit 400 encloses all four side reactors which are shown in FIGS. 1 and 2. In this embodiment, the feed composition exiting from distillation column 36 at a particular stage is taken on line 84 through pump 30′′ and passes through heat exchanger 76 and is inserted on line 402 through inlet 404 into integrated side reactor unit 400. The reacted composition is then exited from a cartridge section of integrated side reactor unit 400 at outlet 406 for repassage on line 408 through heat exchanger 76 and then flows on line 410 to distillation column 36.

In similar fashion, the composition stream is exited from a further stage of distillation column 36 on line 84′, passed through pump 30′′′, and through heat exchanger 76′ for entry on line 412 into a chamber or cartridge of integrated side reactor unit 400 through entry nozzle 414. This then reacts within the appropriate chamber of reactor unit 400 and exits through exit conduit 416. The product stream then passes on exit line 418 for re-entry and passage through heat exchanger 76′ and is re-inserted into distillation chamber 36.

In this manner, one integrated side reactor unit 400 may be used in place of the four side reactors 66, 68, 70, and 72 as provided in the process shown in FIGS. 1 and 2. This reduced number of processing units would reduce the capital costs and improve process operation.

Figure 5:
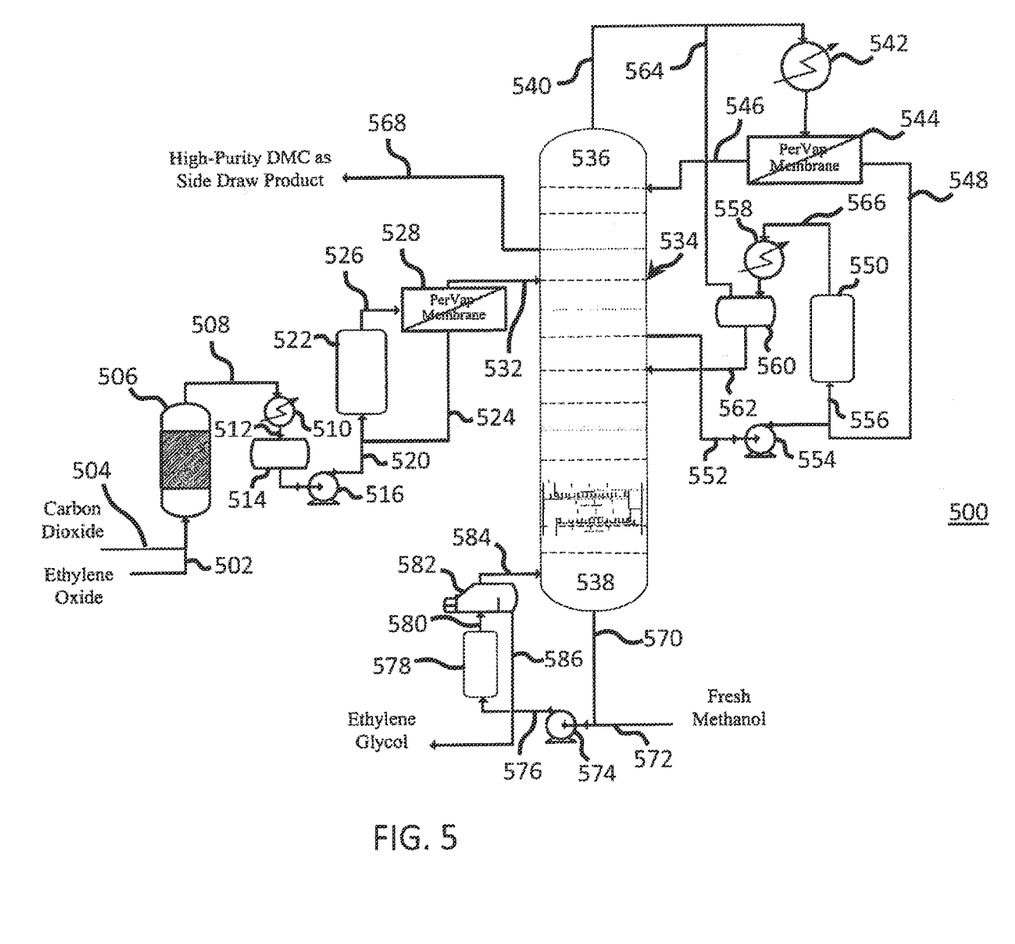
FIG. 5 is a schematic flow diagram for the ethylene oxide-based alkyl carbonate process.

Referring now to FIG. 5, there is shown ethylene based distillation system 500 for producing concentrated dimethyl carbonate. Ethylene oxide on ethylene oxide line 502 is combined with the insert of carbon dioxide on carbon dioxide line 504 and inserted into fixed bed reactor 506. The output of fixed bed reactor 506 is a product stream substantially in vapor form which passes on ethylene carbonate line 508 to condenser 510 where it is condensed and inserted on line 512 to receiver tank 514. Condensed ethylene carbonate is then pumped through pump 516 on line 520 and fed into pre-reactor 522.

The condensed ethylene carbonate is combined with methanol in a recycling process which is combined on recycled methanol line 524.

Reaction within the pre-reactor 522 results in a dimethyl carbonate, ethylene glycol, unreacted methanol and ethylene carbonate exiting on line 526 for entry into pervaporation membrane unit 528 where there is a separation of methanol from the overall composition and returned through recycled methanol line 524 for insert into pre-reactor 522 in combination with the ethylene carbonate passing on line 520. The pervaporation membrane unit 528 separates a portion of the methanol from the product stream exiting on 532 into distillation column 534. The composition passing on exit line 532 includes dimethyl carbonate, ethylene carbonate, ethylene glycol, and some portion of methanol. Distillation column 534 is a standard distillation column having numerous stages. The distillation column 534, as seen in FIG. 5, includes the distillation column upper section 536 and distillation column lower section 538.

Recycling of dimethyl carbonate and unreacted methanol is drawn through dimethyl carbonate and methanol exit line 540 and is drawn into condenser 542 as a vapor wherein it is condensed in condenser 542. The liquid stream is then pumped through the pervaporation membrane unit 544 where the dimethyl carbonate is separated from the methanol. A dimethyl carbonate rich composition exits pervaporation membrane unit 544 and is re-inserted into distillation column upper section 536 through line 546 with the separated methanol being passed on methanol rich line 548 for eventual charging of side reactor 550. This provides for the dimethyl carbonate rich composition to be drawn from the recycling process and inserted into distillation column 534 and results in the rich retentate stream of dimethyl carbonate rich composition to be returned to the column 534 as reflux. In order to further enhance the recycling process, at one or more stages of the distillation column 534, a liquid stream of the dimethyl carbonate, methanol, ethylene glycol, and ethylene carbonate is withdrawn on liquid stream line 552 and passed through pump 554 for combining with the methanol rich composition on line 548 for insert into side reactor 550 on line 556. The reacted composition is then exited from side reactor 550 on side reactor exit line 566 and inserted into heat exchanger 558 and the vapor/liquid is separated in flash tank 560. The liquid composition is then returned to one of the stages of distillation column 534 on line 562. The vapor phase from the flash tank 560 is passed through vapor composition line 564 and combined with the dimethyl carbonate and methanol composition passing on line 540 insert into condenser 542. In this recycling process, a dimethyl carbonate rich composition is inserted into distillation column 534. Through this recycling process, a high purity dimethyl carbonate is withdrawn from distillation column 534 on line 568 for use.

In the process as described, ethylene glycol may be further removed from the ethylene based distillation system 500 as a byproduct. After passage through the various stages of distillation of column 534, ethylene carbonate, ethylene glycol, and perhaps some unreacted methanol, is collected in distillation column lower section 538. The composition is withdrawn from lower section 538 on composition line 570 where it is mixed with fresh methanol on line 572 and inserted through pump 574 to side reactor 576. Fresh methanol line 572 may be either fresh methanol or recycled methanol derived from the recycling process. Pump 574 drives the combined composition entering on line 570 and 572 and inserts the combined composition on line 576 into side reactor 578. Reaction within side reactor 578 provides for a rich ethylene glycol mixture being exited on side reactor exit line 580 with some unreacted methanol. The composition passing on side reactor exit line 580 is inserted into reboiler 582 where volatile products and excess methanol are vaporized and fed back into distillation column 534 on line 584. The liquid ethylene glycol is removed from reboiler 582 on ethylene glycol exit line 586 and is used as a byproduct of the entire process. In this manner, high purity dimethyl carbonate is obtained by withdrawal on line 568 with an ethylene glycol composition being withdrawn on line 586.

For both recycling processes illustrated in FIGS. 1 and 5, the methanol/dimethyl carbonate azeotrope is shown to be broken with a pervaporation membrane unit on the distillate and the methanol is recycled and fed to either singular or multiple side reactors. Pervaporation membrane units as illustrated in FIGS. 1 and 5 are commercially available and pervaporation membranes such as zeolite, cross-linked chitosan and highly fluorinated polymer membranes may be used. However, the pervaporation membrane units shown are for illustrative and descriptive purposes. Other separation techniques for separating and recycle of the excess reactant methanol from the product stream may be used. Such separation methods may include molecular-sieve separation, pressure-swing adsorption, liquid-liquid separation of immiscible liquid mixtures, and heat integrated distillation. All such techniques are well-known in the art.

The side reactors illustrated in FIGS. 1 and 5 may be packed with a commercial heterogeneous catalyst for either process illustrated. Such catalysts may be provided in the form of zirconium dioxide, magnesium (II) oxide, magnesium stearate, calcium (II) oxide, lanthanum (III) oxide, titanium dioxide, calcium chloride, calcium stearate, zinc oxide, zinc acetate dihydrate, zinc carbonate, zinc hydroxide, zinc nitrate hexahydrate, zinc chloride, lead nitrate, lead oxide, dialkyl tin oxide, dialkyl tin methyloxide, or 1,1,3, 3-tetraalkyl-1-methoxy-3-isocyanatodistannoxane. Alkyl may refer to any saturated carbon chain having less than 10 carbons. Differing catalysts may be used on individual side reactors as described previously.

All or a portion of the liquid from a packed section or tray in a respective distillation column may be removed as a liquid side-draw to be fed to an associated side reactor. Fresh or partially purified alcohol from the process recycle streams may be mixed with the side draw prior to entering the side reactor. The particular side reactor feed may be preheated to accelerate the conversion within the side reactor and upon exiting from the side reactor, the effluent may be flashed to remove some portion of the unreacted alcohol or dialkyl carbonate from the product mixture. Reactor conditions are generally within the range of 70° C.-200° C. and may be up to 20-40 atmospheres of pressure to achieve the desired alcohol conversions and dialkyl carbonate selectivity.

Figure 6:
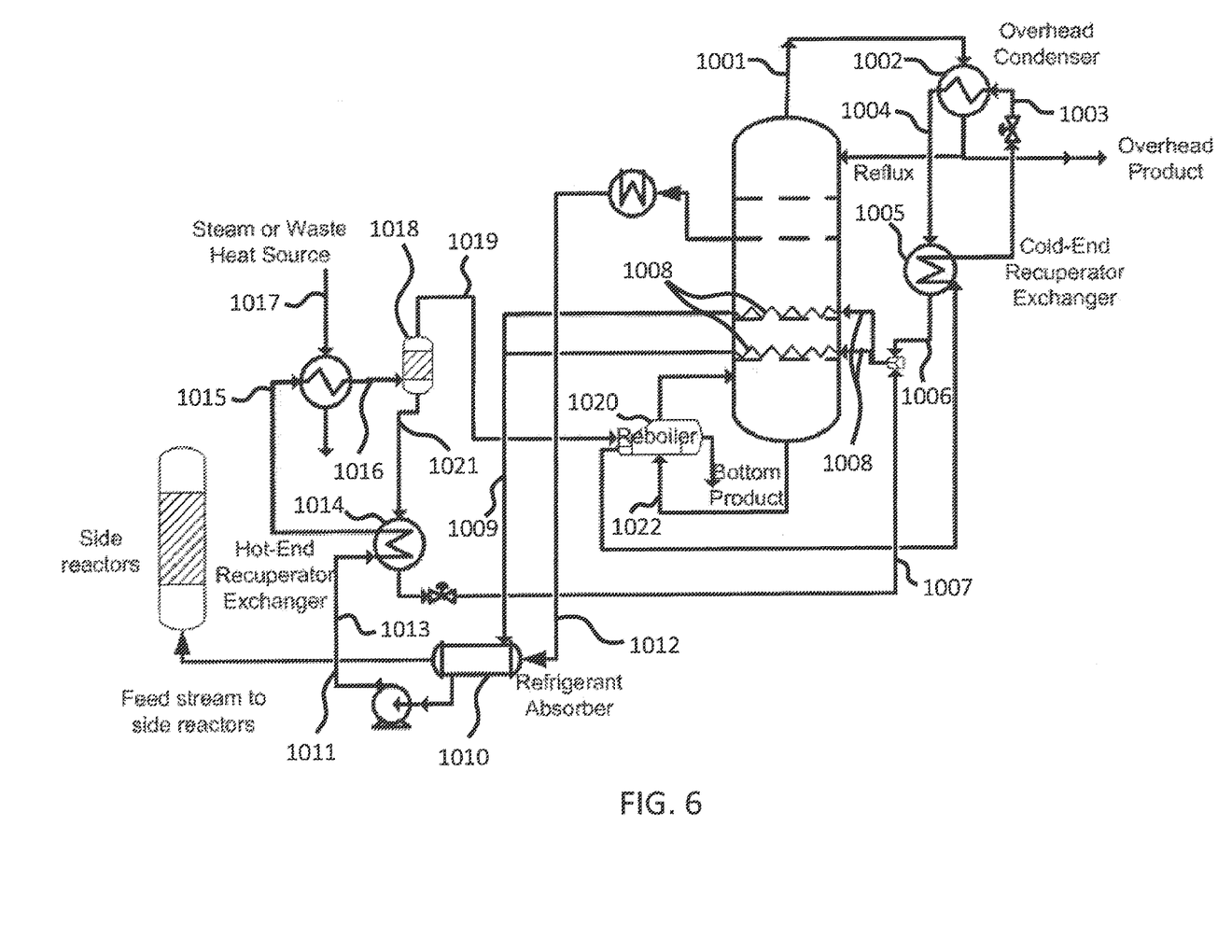
FIG. 6 is a schematic flow diagram of a thermal heat pump for recovery of reject latent heat used in the ammonia-based alkyl carbonate and the ethylene oxide-based alkyl carbonate processes.

Referring now to FIG. 6, there is shown the flow diagram for recovery of reject latent heat from the distillation overhead condenser 1002 that condenses the stream on line 1001 and is used in the above described processes. The reject latent heat is recovered by boiling the refrigerant stream transmitted on feed line 1003. The vapor stream on vapor stream line 1004 exchanges heat in the recuperator 1005 with the incoming liquid stream on line 1022 thereby cooling the stream.

The refrigerant vapor stream on vapor stream line 1006 is combined with the absorbent rich liquid stream on line 1007 from the hot end recuperator 1014. A portion of the refrigerant is absorbed resulting in a higher temperature of the vapor liquid mixture 1008. The mixture 1008 is then fed to the heat transfer device on the thermally active trays 1008 to provide heat to the internal reboilers/heaters. Through the use of providing internal heat, the thermal load of the primary boiler 1020 is reduced thereby reduced with the result of increasing the energy efficiency of the overall system.

The refrigerant-absorbent stream on line 1009 is fed to the refrigerant absorber 1010 for cooling where substantially all of the refrigerant is absorbed in the absorbent. The heat of absorption may be used to preheat feed streams from the distillation column to the side reactors as shown in FIGS. 1 and 5.

The refrigerant-absorbent mixture in liquid form passes on line 1013 and is pressurized and pumped through hot-end recuperator 1014 where the hot absorbent stream on line 1013 is pre-heated.

Waste heat or steam is transmitted on line 1017 provides the primary source for generating refrigerant from the mixture. Vapor on line 1019 and liquid on line 1021 passes to flash tank 1018 where the phases are separated.

The vapor refrigerant at high temperature and pressure provides heat to the re-boiler 1020 of the distillation column. The liquid absorbent stream on line 1021 preheat the incoming absorbent-refrigerant mixture on line 1013. The cooled liquid stream on line 1022 is mixed with the vapor stream on line 1006 for completion of the thermal heat pump cycle. The thermal heat pump system as herein described has been shown to reduce steam consumption by up to 44% in distillation processes of hydrogen peroxide production known in the prior art.

FIG. 7 is a representation of different refrigerant pairs which may be used in the thermal pump. Where low temperature applications are found, it appears that the ammonia-water pair is optimal. At higher temperatures, consideration should be given to an alkitrate-water pair.

Figure 8:
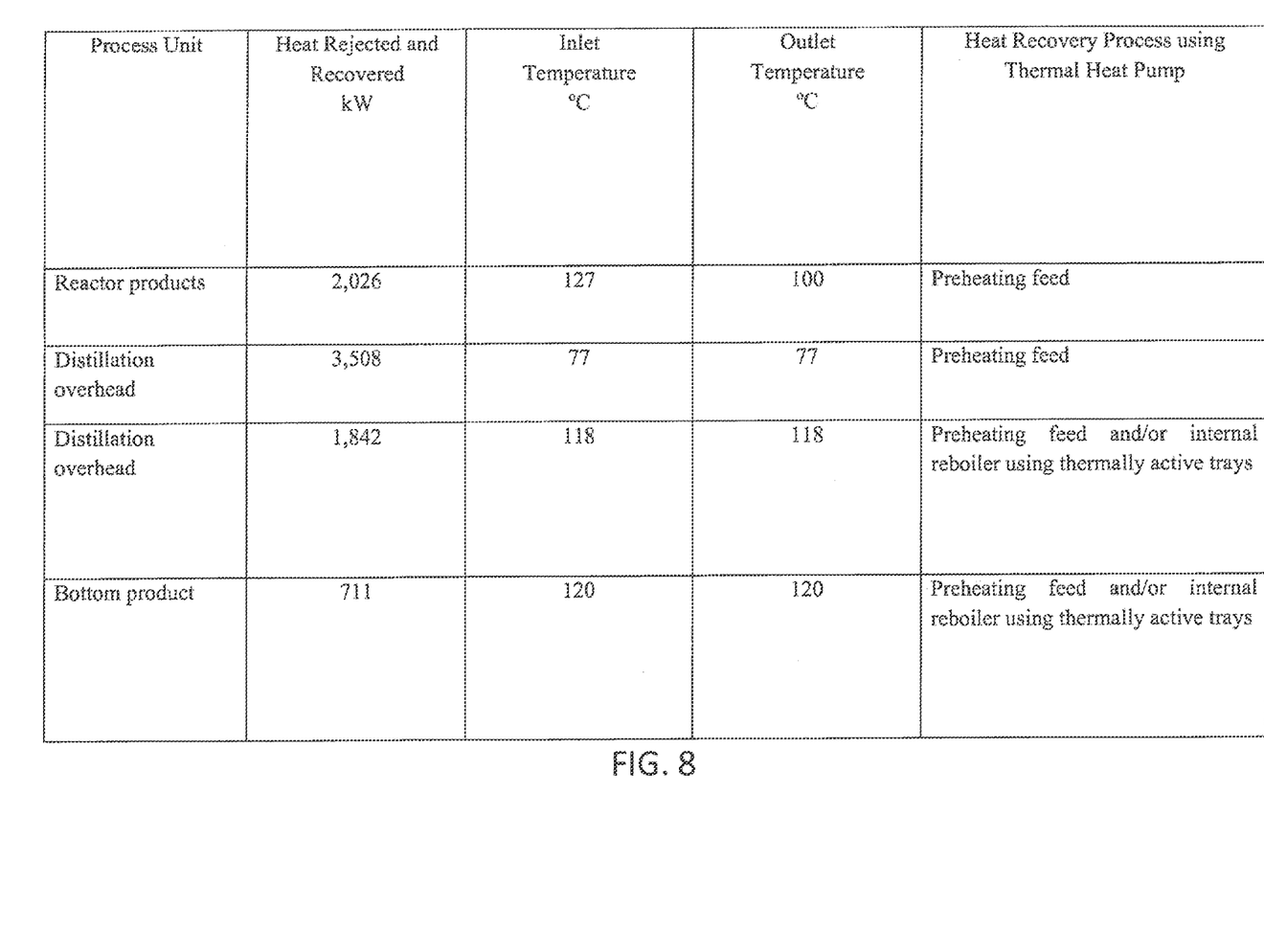

As an example for the process as depicted in FIGS. 1 and 2 a total heat input of 38.4 Kw is found for process conditions shown in FIG. 8. The process was found to reject 28.8 Kw of heat which can be recovered and used in the process shown in FIG. 8. The thermal heat pump requires 9.5 Kw of heat equivalent for recovery and use of the reject heat of 28.8 Kw. The overall resulting energy consumption is reduced from 38.4 Kw to 19.1 Kw representing a sizeable energy improvement.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of elements, steps, or processes may be reversed or interposed, all without departing from the spirit or scope of the invention as defined in the appended claims.

What is claimed is:

1. A method of producing a concentrated dimethyl carbonate composition including the steps of:
   (a) reacting carbon dioxide and ammonia to form urea in a reaction tank;
   (b) inserting said urea into a stirring tank and adding methanol to said stirring tank to produce methyl carbamate and ammonia;
   (c) reacting said methyl carbamate and ammonia with methanol to produce a dimethyl carbonate, methyl carbamate and ammonia mixture;
   (d) establishing a distillation column;
   (e) charging said distillation column with said dimethyl carbonate, ammonia, unreacted methyl carbamate, and unreacted methanol mixture;
   (f) recycling said ammonia from said distillation column to said reaction tank;
   (g) drawing a mixture of dimethyl carbonate, methyl carbamate and methanol from at least a first stage of said distillation column;
   (h) passing said drawn mixture through at least one side methanol reactor for producing a more concentrated dimethyl carbonate composition;
   (i) returning said concentrated dimethyl carbonate to said distillation column; and
   (j) withdrawing a further concentrated dimethyl carbonate composition from a lower section of said distillation column.

2. The method as recited in claim 1 where said distillation column is a partitioned wall distillation column having a first distillation column section and a second distillation column section.

3. The method as recited in claim 1 where the step of recycling said ammonia includes the steps of:
   (a) drawing a mixture of ammonia and unreacted methanol from an upper section of said distillation column;
   (b) condensing said ammonia and unreacted methanol mixture in a condenser;
   (c) charging said reaction tank with said ammonia; and,
   (d) returning at least a portion of said unreacted methanol to said distillation column and said stirring tank.

4. The method as recited in claim 1 including a plurality of side reactors for further purifying said dimethyl carbonate composition.

5. The method as recited in claim 4 further including the following steps:
   (k) enclosing the plurality of side reactors in the form of tubular reactors in a pressure vessel consisting of a shell and flanges;
   (l) loading a catalyst inside each of the tubular reactors;
   (m) dedicating an inlet and an outlet nozzle for each side reactor for connecting to the distillation column; and
   (n) introducing heating or cooling media on the shell side for maintaining optimum reaction temperature.

6. The method as recited in claim 4 where the side reactors charge the further purified dimethyl carbonate into the distillation column below a location in said distillation column where the drawn mixture is passed to said side reactors.

7. The method as recited in claim 2 where the step of returning said concentrated dimethyl carbonate to said distillation column is followed by the step of passing said further concentrated dimethyl carbonate composition through a plurality of distillation stages in said first distillation column section to said lower section of said distillation column.

8. The method as recited in claim 7 including the step of recycling the further concentrated dimethyl carbonate composition through said second distillation column section for reintroducing dimethyl carbonate composition into an upper section of said partitioned distillation column.

9. The method as recited in claim 8 where said step of recycling the further concentrated dimethyl carbonate includes the steps of:

heating the further concentrated dimethyl carbonate in the lower section of said partitioned distillation column and passing the further concentrated dimethyl carbonate with unreacted methanol composition through said second distillation column section to an upper section of said partitioned distillation column.

10. The method as recited in claim 9 where the step of recycling the further concentrated dimethyl carbonate and unreacted methanol composition includes the steps of:

(a) removing said further concentrated dimethyl carbonate and methanol composition from said upper section of said partitioned distillation column; and, (b) separating said dimethyl carbonate and methanol composition; and, (c) returning said dimethyl carbonate to said upper section of said partitioned distillation column.

11. The method as recited in claim 10 where the step of separating includes the steps of:

(a) condensing said further concentrated dimethyl carbonate and unreacted method composition;

(b) passing said condensed further concentrated dimethyl carbonate and methanol composition through a pervaporation membrane unit for removal of unreacted methanol from said further concentrated dimethyl carbonate and methanol composition; and, (c) returning a purified dimethyl carbonate composition to said upper section of said partitioned distillation column.

12. The method as recited in claim 1, wherein recovery of reject and reuse of latent heat is accomplished through the following steps:

(o) using a binary or ternary refrigerant and absorbent mixture;

(p) boiling the binary or ternary refrigerant to recover the reject latent heat from overhead condensers of the dimethyl carbonate process;

(q) absorbing low-pressure vapor generated in step (p) into an absorbent rich solution that releases the heat of absorption;

(r) reusing the released heat within the dimethyl carbonate process;

(s) heating the concentrated refrigerant using waste heat or primary heat to generate refrigerant vapor at high temperature and pressure; and (t) using the high temperature refrigerant vapor generated in step (q) as a heat source for reboilling of the distillation column.

* * * * *